(12) United States Patent
Igarashi

(10) Patent No.: US 10,780,212 B2
(45) Date of Patent: *Sep. 22, 2020

(54) BIOLOGICAL COMPONENT COLLECTION SYSTEM AND FLOW PATH INTERNAL PRESSURE ACQUISITION METHOD

(71) Applicant: TERUMO KABUSHIKI KAISHA, Tokyo (JP)

(72) Inventor: Masatsugu Igarashi, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,477

(22) Filed: Mar. 22, 2019

(65) Prior Publication Data

US 2019/0290825 A1    Sep. 26, 2019

(30) Foreign Application Priority Data

Mar. 26, 2018 (JP) .................. 2018-057410

(51) Int. Cl.
*A61M 1/34* (2006.01)
*G01L 27/00* (2006.01)
(Continued)

(52) U.S. Cl.
CPC .......... *A61M 1/3496* (2013.01); *A61M 1/306* (2014.02); *A61M 1/308* (2014.02);
(Continued)

(58) Field of Classification Search
CPC .............. A61M 1/3693; A61M 1/0209; A61M 1/0272; A61M 1/3496; A61M 2205/3331;
(Continued)

(56) References Cited

U.S. PATENT DOCUMENTS 6,491,656 B1 * 12/2002 Morris ................ A61M 1/3621
604/6.09
8,591,448 B2 * 11/2013 Powers ............... A61M 1/3639
604/4.01
(Continued)

FOREIGN PATENT DOCUMENTS

WO    WO-2004061399 A2 *  7/2004  .......... A61M 1/3639
WO       2011084348 A2      7/2011
(Continued)

*Primary Examiner* — Charles Cooley
(74) *Attorney, Agent, or Firm* — Terumo BCT, Inc. IP Law Dept.

(57) ABSTRACT

A blood component collection system (10) includes a first internal pressure calculation unit (110) adapted to calculate a first internal pressure of a first pressed portion (60) using first calibration curve data (118), a second internal pressure calculation unit (112) adapted to calculate a second internal pressure of a second pressed portion (62) using second calibration curve data (120), and a correction unit (114) adapted to correct the first calibration curve data (118) in a manner so that the first internal pressure becomes equal to the second internal pressure in a state in which operation of a collection and returning pump (100) is stopped during at least one of a collection operation and a returning operation of a first cycle.

2 Claims, 14 Drawing Sheets

(51) Int. Cl.
| | |
|---|---|
| *G01L 13/00* | (2006.01) |
| *B04B 5/04* | (2006.01) |
| *B04B 13/00* | (2006.01) |
| *A61M 1/36* | (2006.01) |
| *A61M 1/38* | (2006.01) |
| *A61M 1/30* | (2006.01) |
| *B04B 11/04* | (2006.01) |
| *A61M 1/02* | (2006.01) |

(52) U.S. Cl.
CPC ........ *A61M 1/3639* (2013.01); *A61M 1/3693* (2013.01); *A61M 1/38* (2013.01); *B04B 5/0428* (2013.01); *B04B 5/0442* (2013.01); *B04B 11/04* (2013.01); *B04B 13/00* (2013.01); *G01L 13/00* (2013.01); *G01L 27/005* (2013.01); *A61M 1/0209* (2013.01); *A61M 2202/0423* (2013.01); *A61M 2205/123* (2013.01); *A61M 2205/125* (2013.01); *A61M 2205/3331* (2013.01); *A61M 2205/702* (2013.01); *A61M 2205/7545* (2013.01)

(58) Field of Classification Search
CPC ...... A61M 2205/50; A61M 2202/0415; A61M 2205/332; A61M 1/0218; A61M 1/38; A61M 2205/125; A61M 1/306; A61M 1/3639; A61M 1/308; A61M 2205/7545; A61M 2202/0423; A61M 2205/123; A61M 2205/702; B04B 11/04; B04B 7/08; B04B 11/00; B04B 2005/0435; B04B 5/0428; B04B 7/02; B04B 13/00; B04B 5/0442; G16H 10/40; G01L 27/005
See application file for complete search history.

(56) References Cited

U.S. PATENT DOCUMENTS

| | | | |
|---|---|---|---|
| 10,352,950 B2* | 7/2019 | Ochiai | G01N 21/27 |
| 10,413,653 B2* | 9/2019 | Case | A61M 1/3639 |
| 2010/0152013 A1* | 6/2010 | Eberle | B04B 5/0428 494/10 |
| 2010/0292628 A1* | 11/2010 | Powers | A61M 1/3639 604/6.01 |
| 2016/0243300 A1* | 8/2016 | Nackaerts | A61M 1/3693 |
| 2019/0038197 A1* | 2/2019 | Igarashi | A61B 5/150251 |
| 2019/0046710 A1* | 2/2019 | Kusters | A61M 1/306 |
| 2019/0231949 A1* | 8/2019 | Igarashi | A61M 1/0236 |
| 2019/0290822 A1* | 9/2019 | Igarashi | A61M 1/267 |
| 2019/0290825 A1* | 9/2019 | Igarashi | A61M 1/38 |
| 2019/0290830 A1* | 9/2019 | Igarashi | A61M 1/3607 |
| 2019/0290831 A1* | 9/2019 | Igarashi | B04B 11/02 |
| 2020/0164135 A1* | 5/2020 | Igarashi | B04B 5/0442 |
| 2020/0164136 A1* | 5/2020 | Igarashi | A61M 1/0218 |
| 2020/0164137 A1* | 5/2020 | Igarashi | B04B 5/0442 |
| 2020/0197582 A1* | 6/2020 | Igarashi | A61M 1/302 |
| 2020/0197583 A1* | 6/2020 | Igarashi | A61M 1/30 |

FOREIGN PATENT DOCUMENTS

| | | | |
|---|---|---|---|
| WO | WO-2018230155 A1 * | 12/2018 | ............ A61M 1/302 |
| WO | WO-2018230156 A1 * | 12/2018 | ............ A61M 1/302 |
| WO | WO-2018230545 A1 * | 12/2018 | .......... A61M 1/0218 |

* cited by examiner

BIOLOGICAL COMPONENT COLLECTION SYSTEM AND FLOW PATH INTERNAL PRESSURE ACQUISITION METHOD

TECHNICAL FIELD

The present invention relates to a biological component collection system equipped with a biological component collection device configured to be attachable to a separation device, as well as to a flow path internal pressure acquisition method.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining blood components are returned again into the donor's body.

In Japanese Laid-Open Patent Publication No. 2013-514863 (PCT), a blood component collection system is disclosed in which blood platelets are collected by centrifugally separating whole blood that is extracted from a blood donor.

Such a blood component collection system includes a blood collection circuit set, which forms a circuit through which blood or blood components to be treated flow, and a centrifugal separation device (blood component separation device) in which the blood collection circuit set is mounted.

The blood collection circuit set is equipped with a blood collection line having a blood collecting needle, a band-shaped channel (separator) into which whole blood is introduced, a plurality of bags for accommodating blood components, etc., and a cassette connected through a plurality of tubes to the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separation device.

SUMMARY OF INVENTION

In such a blood component collection system, in order to ascertain whether or not the blood component separation device is operating properly, it is necessary to measure and monitor the pressure (circuit internal pressure) inside the blood collection circuit. Similar problems also occur in biological component collection systems other than blood component collection systems.

The present invention has been devised taking into consideration the aforementioned problems, and has the object of providing a biological component collection system, and a flow path internal pressure acquisition method, which are capable of accurately measuring the circuit internal pressure.

In order to achieve the aforementioned object, a biological component collection system according to the present invention is equipped with a separation device having a first load detecting unit and a second load detecting unit and which is adapted to separate a biological component from a biological liquid, a biological component collection device configured to be attachable to the separation device and having a biological liquid line formed therein through which the biological liquid or the biological component flows, and a collection and returning pump, the biological component collection system performing a plurality of times a cycle including a collection operation for collecting a desired biological component in the biological liquid by allowing the biological liquid to flow from a donor through the biological liquid line to the separation device under an action of the collection and returning pump, and a returning operation for returning remaining biological components to the donor from the separation device through the biological liquid line under the action of the collection and returning pump, wherein the biological component collection device is formed of a soft material and has a line forming member defining the biological liquid line that is formed by a wall portion, a part of the wall portion of the line forming member includes a first applied load measurement unit adapted to measure a load applied to the wall portion of the line forming member by the first load detecting unit, in a device mounted state in which the biological component collection device is mounted in the separation device, and a second applied load measurement unit adapted to measure a load applied to the wall portion of the line forming member by the second load detecting unit in the device mounted state, the separation device comprising a first internal pressure calculation unit adapted to calculate a first internal pressure of the first applied load measurement unit on the basis of a first detection signal from the first load detecting unit and first internal pressure calculation data, a second internal pressure calculation unit adapted to calculate a second internal pressure of the second applied load measurement unit on the basis of a second detection signal from the second load detecting unit and second internal pressure calculation data, and a correction unit adapted to correct the first internal pressure calculation data in a manner so that the first internal pressure calculated by the first internal pressure calculation unit becomes equal to the second internal pressure calculated by the second internal pressure calculation unit, in a state in which operation of the collection and returning pump is stopped in at least one of during the collection operation and during the returning operation of a first cycle.

In accordance with such a configuration, the first internal pressure calculation data is corrected in a manner so that the first internal pressure calculated by the first internal pressure calculation unit becomes equal to the second internal pressure calculated by the second internal pressure calculation unit, in a state in which operation of the collection and returning pump is stopped in at least one of during the collection operation and during the returning operation of the first cycle. Consequently, by the corrected first internal pressure calculation data, it is possible to cancel any measurement error of the first detection signal due to creep deformation or the like occurring in the first applied load measurement unit. Accordingly, the circuit internal pressure can be accurately measured by the first internal pressure calculation unit.

In the above-described biological component collection system, a flow path cross-sectional area of the second applied load measurement unit may be greater than a flow path cross-sectional area of the first applied load measurement unit, the first load detecting unit may press on a wall portion of the first applied load measurement unit in the device attached state, and the second load detecting unit may press on a wall portion of the second applied load measurement unit in the device attached state.

In accordance with such a configuration, the flow path cross-sectional area of the second applied load measurement unit is greater than the flow path cross sectional area of the first applied load measurement unit. Therefore, the first internal pressure calculation unit is capable of calculating the first internal pressure (positive pressure and negative pressure) of the first applied load measurement unit. However, in the first applied load measurement unit, it is more likely for creep deformation to occur than in the second applied load measurement unit. Therefore, in particular, in the collection operation and the returning operation of the first cycle, a measurement error of the first detection signal due to creep deformation of the first applied load measurement unit is likely to occur. On the other hand, since the second applied load measurement unit is less likely to suffer from creep deformation than the first applied load measurement unit, the second applied load measurement unit is capable of relatively accurately calculating the second internal pressure (positive pressure). In addition, since the first internal pressure calculation data is corrected in a manner so that the first internal pressure calculated by the first internal pressure calculation unit becomes equal to the second internal pressure calculated by the second internal pressure calculation unit, it is possible to measure the circuit internal pressure with high accuracy.

In the above-described biological component collection system, the biological liquid line may include a collection line in which the biological liquid is made to flow at a time of the collection operation, and a returning line in which the biological component is made to flow at a time of the returning operation, and the line forming member may include a first line forming member in which the collection line is formed, and which includes the first applied load measurement unit, and a second line forming member in which the returning line is formed, and which includes the second applied load measurement unit.

In accordance with such a configuration, it is possible to suppress any influence that deformation of the first applied load measurement unit exerts on the second applied load measurement unit.

In the above-described biological component collection system, the second applied load measurement unit may be a filter accommodating unit in which there is accommodated a filter member configured to separate a predetermined component from within the biological components at the time of the returning operation.

In accordance with such a configuration, since the second applied load measurement unit can also serve in a dual manner as the filter accommodating unit, the structure of the biological component collection device can be made compact. Further, the number of operations performed by the operator (a process to attach the filter member) is reduced, and usability is enhanced.

In the above-described biological component collection system, the biological liquid line may further comprise a first coupling member adapted to couple one end portion of the collection line and one end portion of the returning line to each other, and a second coupling member adapted to couple another end portion of the collection line and another end portion of the returning line to each other.

In accordance with such a configuration, the structure of the biological component collection device can be made more compact.

In the above-described biological component collection system, prior to performing the collection operation of the first cycle after having performed a priming process of the biological liquid line by operating the collection and returning pump, the correction unit may correct the first internal pressure calculation data in a manner so that the first internal pressure calculated by the first internal pressure calculation unit becomes equal to the second internal pressure calculated by the second internal pressure calculation unit in a state in which the collection and returning pump is stopped.

In accordance with such a configuration, the circuit internal pressure can be measured more accurately.

A biological component collection system according to the present invention is equipped with a separation device adapted to separate a biological component from a biological liquid, a biological component collection device configured to be attachable to the separation device and having a biological liquid line formed therein through which the biological liquid or the biological component flows, and a collection and returning pump, the biological component collection system performing a plurality of times a cycle including a collection operation for collecting a desired biological component in the biological liquid by allowing the biological liquid to flow from a donor through the biological liquid line to the separation device under an action of the collection and returning pump, and a returning operation for returning remaining biological components to the donor from the separation device through the biological liquid line under the action of the collection and returning pump, wherein the collection and returning pump is temporarily stopped in at least one of during the collection operation and during the returning operation of a first cycle.

In accordance with such a configuration, it is possible to correct the internal pressure calculation data that is used when calculating the internal pressure of the biological liquid line, in a state in which operation of the collection and returning pump is stopped in at least one of during the collection operation and during the returning operation of the first cycle. Therefore, the circuit internal pressure can be accurately measured.

In a flow path internal pressure acquisition method according to the present invention, there is used a biological component collection system equipped with a separation device having a first load detecting unit and a second load detecting unit and adapted to separate a biological component from a biological liquid, a biological component collection device configured to be attachable to the separation device and having a biological liquid line formed therein through which the biological liquid or the biological component flows, and a collection and returning pump, the biological component collection system performing a plurality of times a cycle including a collection operation for collecting a desired biological component in the biological liquid by allowing the biological liquid to flow from a donor through the biological liquid line to the separation device under an action of the collection and returning pump, and a returning operation for returning remaining biological components to the donor from the separation device through the biological liquid line under the action of the collection and returning pump, wherein the biological component collection device is formed of a soft material and has a line forming member defining the biological liquid line that is formed by a wall portion, a part of the wall portion of the line forming member includes a first applied load measurement unit adapted to measure a load applied to the wall portion of the line forming member by the first load detecting unit, in a device mounted state in which the biological component collection device is mounted in the separation device, and a second applied load measurement unit adapted to measure a load applied to the wall portion of the line forming member by the second load detecting unit in the device mounted state, the flow path internal pressure acquisition method comprising a collection and returning determination step of determining whether or not it is during a collection operation or during a returning operation of a first cycle, and a calibration step of performing calibration of first internal pressure calculation data, for a case in which, in the collection and returning determination step, it is determined that it is during the collection operation or during the returning operation of the first cycle, and in the calibration step, there are performed a pump stopping step of stopping the collection and returning pump, a first internal pressure calculation step of calculating a first internal pressure of the first applied load measurement unit on the basis of a first detection signal from the first load detecting unit and first internal pressure calculation data while the collection and returning pump is stopped, a second internal pressure calculation step of calculating a second internal pressure of the second applied load measurement unit on the basis of a second detection signal from the second load detecting unit and second internal pressure calculation data while the collection and returning pump is stopped, and a correction step of correcting the first internal pressure calculation data in a manner so that the first internal pressure calculated by the first internal pressure calculation step becomes equal to the second internal pressure calculated by the second internal pressure calculation step.

In the above-described flow path internal pressure acquisition method, there may further be performed a pre-collection calibration step of performing calibration of the first internal pressure calculation data prior to performing the collection operation of the first cycle after having performed a priming process of the biological liquid line by operating the collection and returning pump, wherein, in the pre-collection calibration step, the same processes as those of the calibration step may be performed.

In accordance with the biological component collection system and the flow path internal pressure acquisition method of the present invention, it is possible to accurately measure the circuit internal pressure.

DESCRIPTION OF EMBODIMENTS

Preferred embodiments of a biological component collection system and a flow path internal pressure acquisition method according to the present invention will be presented and described in detail below with reference to the accompanying drawings.

Figure 1:
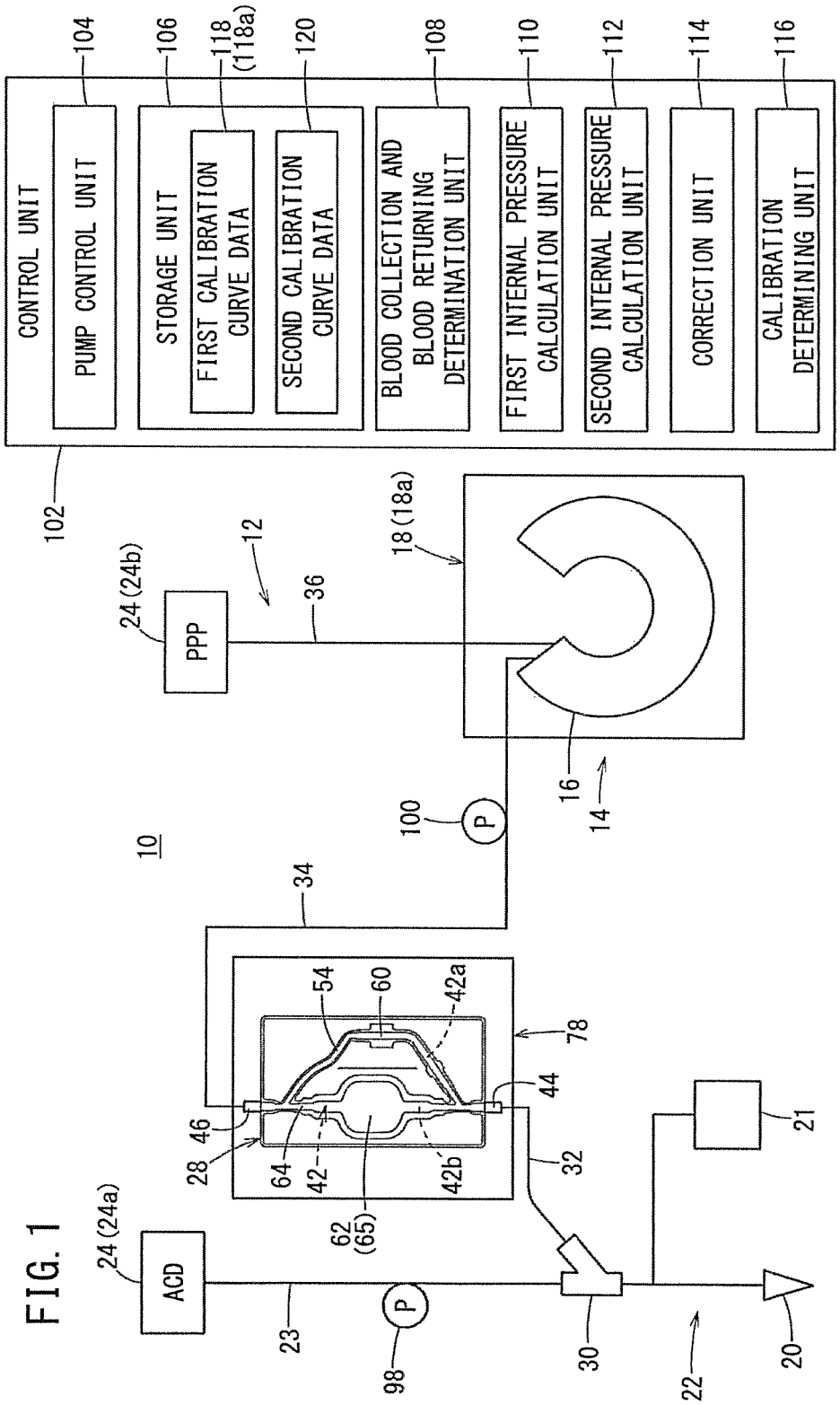
FIG. 1 is a schematic diagram of a blood component collection system according to an embodiment of the present invention.

As shown in FIG. 1, a blood component collection system 10, which is one form of a biological component collection system according to the present invention, is constituted as a blood apheresis system, in which blood (whole blood) is continuously extracted from a blood donor and subjected to centrifugal separation outside the body, whereby a specific blood component (in the present embodiment, plasma (platelet poor plasma: PPP)) is collected, and the remaining blood components are returned to the blood donor. In the present embodiment, the blood component is a biological component, and the blood is a biological liquid (a liquid containing at least one biological component).

First, an outline description will be given of the blood component collection system 10 shown in FIG. 1. The blood component collection system 10 is equipped with a blood collection circuit set 12 for enabling storage and flow of blood components therein, a centrifugal separation device 14 (one form of a blood component separation device or a separation device) that applies a centrifugal force to the blood collection circuit set 12. The blood collection circuit set 12 includes a blood treatment unit 16 (biological liquid treatment unit) in which whole blood that is removed from the blood donor is centrifugally separated into a plurality of blood components. The centrifugal separation device 14 is equipped with a centrifuge unit 18 having a rotor 18a for applying a centrifugal force to the blood treatment unit 16. The blood treatment unit 16 is capable of being mounted in the centrifuge unit 18.

The blood collection circuit set 12 is discarded every time that it is used in order to prevent contamination and ensure sanitation. The blood collection circuit set 12 includes a blood collection and blood returning unit 22 having a blood collecting needle 20 and an initial flow blood collection bag 21, the blood treatment unit 16, a plurality of bags 24, and a blood component collection cassette 28 (hereinafter referred to as a "cassette 28") serving as a biological component collection device to which the aforementioned elements are connected via tubes. The plurality of bags 24 include an ACD solution bag 24a containing an ACD solution which is an anticoagulant, and a PPP bag 24b for storing the plasma (platelet poor plasma).

The blood collection and blood returning unit 22 is connected to the ACD solution bag 24a and the cassette 28 via a tube connector 30. The ACD solution bag 24a is connected to the tube connector 30 via an ACD solution transfer tube 23.

The cassette 28 is connected to the blood collection and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
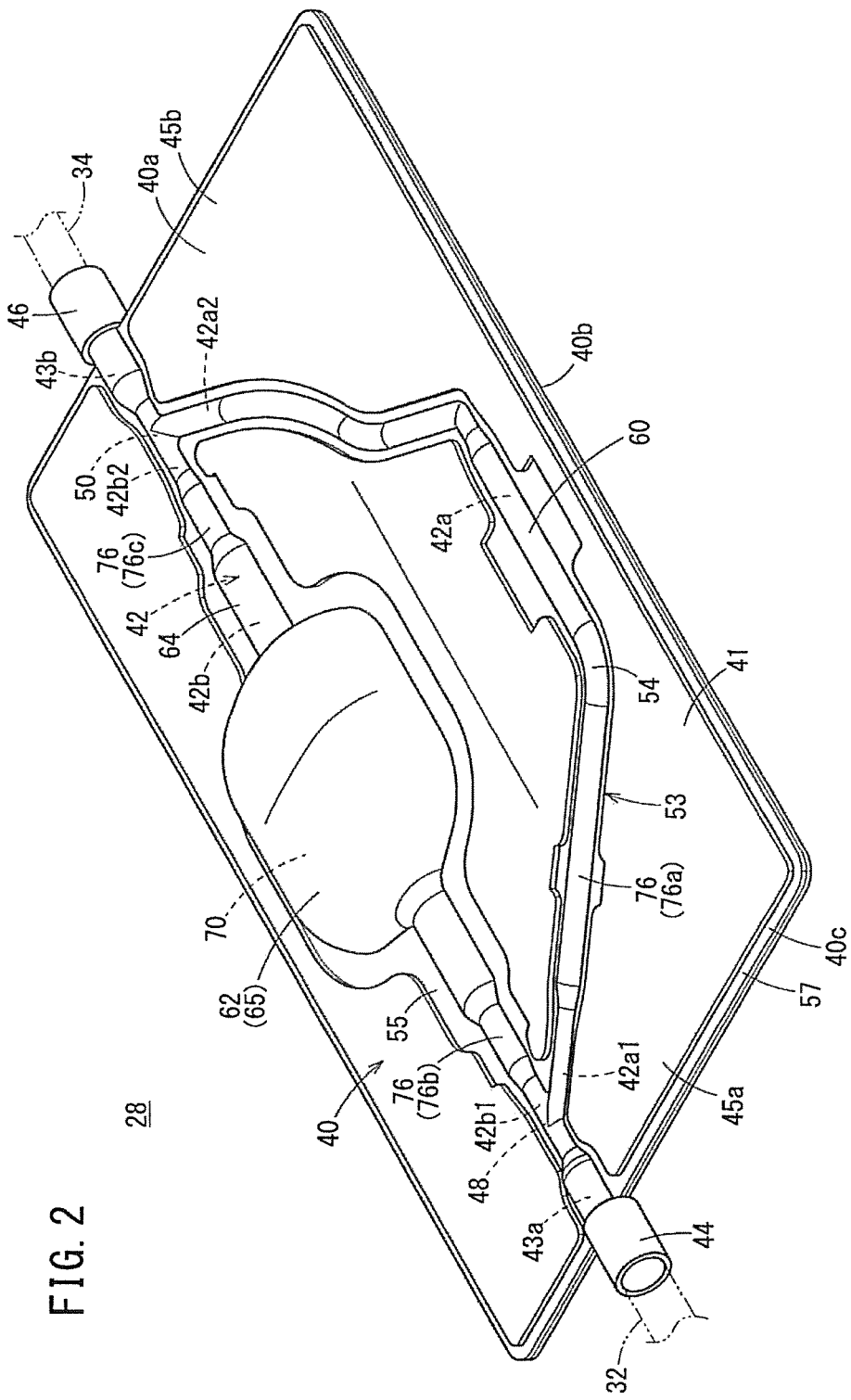
FIG. 2 is a perspective view of a blood component collection cassette.

As shown in FIG. 2, the cassette 28 is provided with a cassette main body 40 in which a blood line 42 (biological liquid line) is formed through which blood or blood components flow. The cassette main body 40 is formed in a rectangular shape as viewed in plan. The cassette main body 40 is formed of a soft material. For the soft material that constitutes the cassette main body 40, the same material is used over the entirety of the cassette main body 40. Moreover, the cassette main body 40 may be constituted from a plurality of different materials. More specifically, the cassette main body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a plasticizer for vinyl chloride, there may be cited diisononylcyclohexane-1,2-dicarboxylate, bis-2-ethylhexyl phthalate, and the like.

The blood line 42 is formed between the first sheet 40a and the second sheet 40b. Fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like). Further, a first port member 44 and a second port member 46, which are made of a hard material (for example, polypropylene, polycarbonate, or the like), are disposed on an outer peripheral edge portion 40c of the cassette main body 40.

The first port member 44 is provided at a first end portion 45a, which is one longitudinal end portion of the rectangular cassette main body 40, and is connected to a first port 43a provided on one end side of the blood line 42. The second port member 46 is provided at a second end portion 45b, which is another longitudinal end portion of the cassette main body 40, and is connected to a second port 43b provided on the other end side of the blood line 42. The donor side tube 32 is connected to the first port member 44, and the treatment unit side tube 34 is connected to the second port member 46.

According to the present embodiment, the first port member 44 and the second port member 46 are arranged on the same straight line along the longitudinal direction of the rectangular cassette main body 40. It should be noted that the first port member 44 and the second port member 46 need not necessarily be arranged on the same straight line.

The blood line 42 which is formed in the cassette main body 40 includes a blood collection line 42a (collection line) through which the blood is made to flow at a time of blood collection, and a blood returning line 42b (returning line) through which the blood components are made to flow at a time that the blood is returned. One end portion 42a1 of the blood collection line 42a and one end portion 42b1 of the blood returning line 42b are connected mutually via a first coupling member 48. Another end portion 42a2 of the blood collection line 42a and another end portion 42b2 of the blood returning line 42b are connected mutually via a second coupling member 50.

The blood collection line 42a and the blood returning line 42b extend at least partially in parallel with each other. The first coupling member 48 and the second coupling member 50 each constitute parts of the blood line 42.

In the cassette main body 40, sealed portions 55 in the form of fusion-bonded locations are formed along the blood line 42 on both sides of the blood line 42. Further, a sealed portion 57 is formed along the outer peripheral edge portion 40c, on the outer peripheral edge portion 40c of the cassette main body 40. In the cassette main body 40 (excluding the convex portion that forms the blood line 42), locations other than the sealed portions 55 and 57 are non-sealed portions where the first sheet 40a and the second sheet 40b are not fusion bonded to each other. Since the sealed portions 55 are subjected to pressure during formation thereof, the sealed portions 55 are smaller in thickness than the non-sealed portions, and are recessed with respect to the non-sealed portions. Stated otherwise, the non-sealed portions protrude in the thickness direction with respect to the sealed portions 55.

Within the cassette main body 40, even when there is no positive pressure acting within the blood line 42, the wall portions that form the blood line 42 bulge in convex shapes in the thickness direction of the cassette 28 on both side surfaces of the cassette main body 40. Accordingly, the blood line 42 is a flow path which is opened in its natural state. When pressed by an external force, the wall portions can be elastically deformed in directions to close the blood line 42 at the pressed locations thereof.

The cassette main body 40 comprises a line forming member 53 that forms the blood line 42. The line forming member 53 includes a first line forming member 54 that forms the blood collection line 42a. In the first line forming member 54, a first pressed portion 60 (first applied load measurement unit) is provided, which is pressed, in a cassette attached state in which the cassette 28 is attached to the centrifugal separation device 14, by a later-described first load detecting unit 88 (see FIG. 3) that is installed in the centrifugal separation device 14. The first pressed portion 60 constitutes a part of the blood line 42. Accordingly, the first pressed portion 60 bulges out in the thickness direction of the cassette main body 40 from a sheet surface 41 (base surface) of the cassette main body 40.

The line forming member 53 includes a second line forming member 64 that forms the blood returning line 42b. In the second line forming member 64, a second pressed portion 62 (second applied load measurement unit) is provided, which is pressed, in the cassette attached state, by a later-described second load detecting unit 90 (see FIG. 3) that is installed in the centrifugal separation device 14. The second pressed portion 62 constitutes a part of the blood line 42. Accordingly, the second pressed portion 62 bulges out in the thickness direction of the cassette main body 40 from the sheet surface 41 of the cassette main body 40.

The second pressed portion 62 constitutes a filter accommodating unit 65. The filter accommodating unit 65 accommodates a filter member 70 for separating predetermined components (clotted blood or blood clumps) contained within the blood components.

On the cassette 28, there are provided a plurality of clamp action members 76 (76a to 76c) on which a plurality of clamps 72 (72a to 72c) (see FIG. 3), which are flow path opening/closing mechanisms provided in the centrifugal separation device 14, act. When the cassette 28 is installed in the centrifugal separation device 14, the clamp action members 76 abut against or are placed in facing relation to their corresponding clamps 72. More specifically, the clamp action member 76a is disposed at a location forming a side of the first port member 44 of the blood collection line 42a in the cassette 28. The clamp action members 76b and 76c are disposed respectively at locations forming both sides of the second pressed portion 62 within the blood returning line 42*b*.

Moreover, the flow path structure formed in the cassette 28, and the number and arrangement of the bags 24 that are provided are not limited to the configurations shown and described above, but may be modified in accordance with the type of blood components to be collected, the method of use, and the like.

In a method for manufacturing the cassette 28 having the above-described configuration, there are included a molding step in which the first sheet 40*a* and the second sheet 40*b* are superimposed on each other, and the first sheet 40*a* and the second sheet 40*b* are fusion bonded together so as to form the blood line 42 between the first sheet 40*a* and the second sheet 40*b*, to thereby mold the cassette 28 equipped with the cassette main body 40, and a sterilization step of sterilizing the cassette 28 obtained by the aforementioned molding step.

In the molding step, for example, sheet-shaped materials are fed out from two material rolls on which there are wound, respectively, sheet materials that serve as the materials for the first sheet 40*a* and the second sheet 40*b*, and the assembly components (the filter member 70, the first port member 44, the second port member 46) are supplied together therewith to a joining device such as a high-frequency fusion bonding device or the like. The joining device is equipped with upper and lower molds, and by carrying out blow molding while the two sheet-shaped materials are joined together with the assembly components, the cassette 28 is molded with the blood line 42 formed therein. In this case, the tubes 32 and 34 may be connected at the time that the cassette 28 is molded in the joining device.

In the sterilization step, the entirety of the blood collection circuit set 12 including the plurality of bags 24 (ACD solution bag 24*a*, etc.) may be sterilized. Consequently, the blood collection circuit set 12 can be sterilized efficiently.

In FIG. 1, the centrifugal separation device 14 is a device that is used repeatedly during blood component collection, and is provided, for example, in a medical facility, a blood collection vehicle, or the like. The centrifugal separation device 14 is equipped with the centrifuge unit 18 having the rotor 18*a*, and a cassette mounting unit 78 configured in a manner so that the cassette 28 of the blood collection circuit set 12 is capable of being attached thereto.

Figure 3:
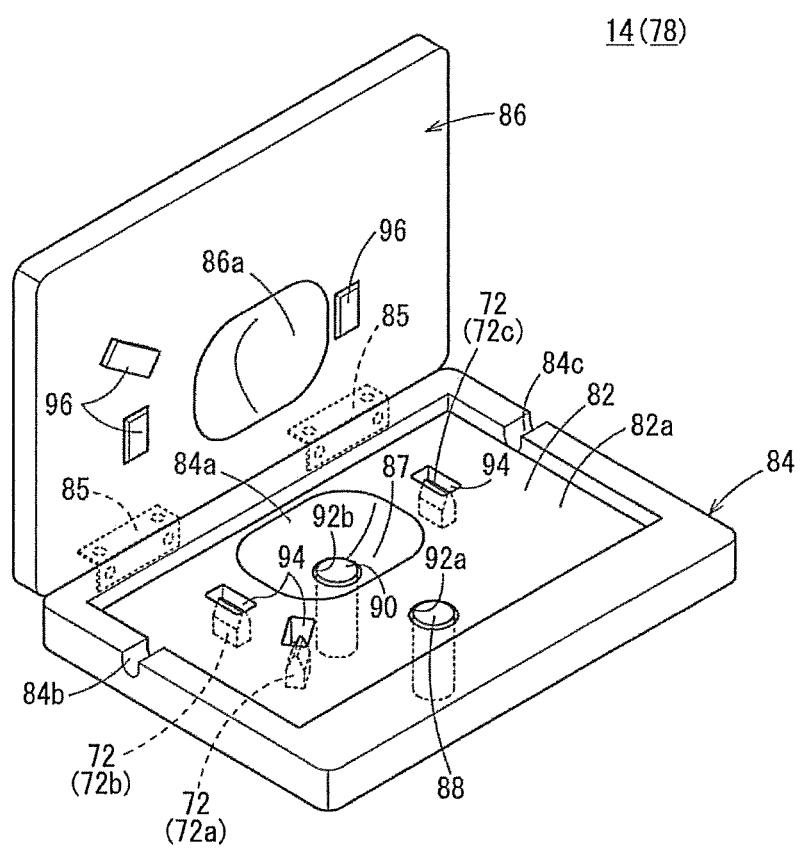
FIG. 3 is a perspective view of a cassette mounting unit.

As shown in FIG. 3, the cassette mounting unit 78 includes an attachment base 84 having a cassette mounting groove 82 formed therein, a lid 86 which can be opened and closed and is configured in a manner so as to cover the attachment base 84 when closed, a first load detecting unit 88 capable of pressing the first pressed portion 60 (see FIG. 2) of the cassette 28, a second load detecting unit 90 capable of pressing the second pressed portion 62 (see FIG. 2) of the cassette 28, and a plurality of clamps 72 configured to be capable of pressing the clamp action members 76 (see FIG. 2) of the cassette 28.

A first port arrangement groove 84*b* into which the first port member 44 of the cassette 28 can be arranged, and a second port arrangement groove 84*c* into which the second port member 46 of the cassette 28 can be arranged are provided on the outer peripheral portion of the attachment base 84. The first port arrangement groove 84*b* and the second port arrangement groove 84*c* are in communication with the cassette mounting groove 82.

The lid 86 is connected in a rotatable manner to the attachment base 84 via a hinge 85. When the lid 86 is closed with the cassette 28 being held in the cassette mounting groove 82 of the attachment base 84, the cassette 28 is sandwiched between the attachment base 84 and the lid 86. On the attachment base 84 and the lid 86, there are respectively provided concave portions 84*a*, 86*a* in which the filter accommodating unit 65 of the cassette 28 can be received. Consequently, the cassette 28 is appropriately retained between the attachment base 84 and the lid 86, while also preventing the filter accommodating unit 65 from being crushed. Further, the concave portions 84*a*, 86*a* prevent the filter accommodating unit 65 from bulging excessively.

The first load detecting unit 88 is inserted into a first through hole 92*a* provided in the attachment base 84, together with being exposed in the cassette mounting groove 82. An upper surface of the first load detecting unit 88 protrudes from a bottom surface 82*a* of the cassette mounting groove 82. The second load detecting unit 90 is inserted into a second through hole 92*b* provided in a bottom surface 87 of the concave portion 84*a*, together with being exposed in the concave portion 84*a*. An upper surface of the second load detecting unit 90 protrudes from the bottom surface 87 of the concave portion 84*a*. The protruding height of the first load detecting unit 88 from the bottom surface 82*a*, and the protruding height of the second load detecting unit 90 from the bottom surface 87 are the same as each other. The first load detecting unit 88 and the second load detecting unit 90 are constituted from load cells, for example.

The plurality of clamps 72 (72*a* to 72*c*) are capable of being advanced and retracted in the thickness direction of the cassette 28 in a state in which the cassette 28 is retained in the cassette mounting groove 82, and are disposed corresponding to the arrangement of the plurality of clamp action members 76 (76*a* to 76*c*) provided on the cassette 28. The plurality of clamps 72 are capable of pressing the plurality of clamp action members 76, respectively, via a plurality of holes 94 that open on the bottom surface 82*a* of the cassette mounting groove 82. When closed, a plurality of projections 96 are provided on the lid 86 at positions corresponding to the plurality of holes 94 (clamps 72).

At a time that the clamp action members 76 are not being pressed by the clamps 72 in a state in which the cassette 28 is mounted in the cassette mounting unit 78, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette main body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a collection and returning pump 100 which acts on the treatment unit side tube 34 that is connected to the cassette 28. The ACD solution transfer pump 98 is a pump that transfers the ACD solution from the ACD solution bag 24*a* to the cassette 28 and the blood treatment unit 16 via the ACD solution transfer tube 23. The collection and returning pump 100 is a pump for transferring blood or blood components. Stated otherwise, the collection and returning pump 100 is a pump that transfers blood from the blood donor to the blood treatment unit 16, and together therewith, transfers the blood from the blood treatment unit 16 back to the blood donor.

The ACD solution transfer pump 98 and the collection and returning pump 100 are constituted, for example, by a roller pump or a finger pump.

The centrifugal separation device 14 further includes a control unit 102. The control unit 102 is a computation device including a microcomputer, and has a CPU (central processing unit), and a ROM, a RAM, etc., serving as memories, wherein by reading out and executing programs stored in the ROM, the CPU functions as various function realizing units (function realizing means). Moreover, the various function realizing units may be constituted by function realizing devices in the form of hardware.

The control unit 102 controls operations of the above-described plurality of clamps 72. The control unit 102 comprises a pump control unit 104, a storage unit 106, a blood collection and blood returning determination unit 108 (collection and returning determination unit), a first internal pressure calculation unit 110, a second internal pressure calculation unit 112, a correction unit 114, and a calibration determining unit 116. The pump control unit 104 controls the operations of the ACD solution transfer pump 98 and the collection and returning pump 100.

First calibration curve data 118 (first internal pressure calculation data) and second calibration curve data 120 (second internal pressure calculation data) are stored in the storage unit 106. The first calibration curve data 118 are data of a linear function indicative of a relationship between a first detection signal (load) from the first load detecting unit 88 and a first internal pressure of the first pressed portion 60. The second calibration curve data 120 are data of a linear function indicative of a relationship between a second detection signal (load) from the second load detecting unit 90 and a second internal pressure of the second pressed portion 62. The first calibration curve data 118 and the second calibration curve data 120 can be obtained in advance by experiment or analysis.

The blood collection and blood returning determination unit 108 determines whether or not it is during a blood collection operation or during a blood returning operation of a first cycle. More specifically, the blood collection and blood returning determination unit 108 determines that it is during the blood collection operation or during the blood returning operation of the first cycle, for example, on the basis of a number of operations of the collection and returning pump 100 after having received an instruction to start blood component collection.

The first internal pressure calculation unit 110 calculates the first internal pressure on the basis of the first detection signal and the first calibration curve data 118 (or the first calibration curve data 118a for which the intercept thereof has been corrected). The second internal pressure calculation unit 112 calculates the second internal pressure on the basis of the second detection signal and the second calibration curve data 120. The correction unit 114 corrects the intercept of the first calibration curve data 118 in a manner so that the first internal pressure calculated by the first internal pressure calculation unit 110 becomes equal to the second internal pressure calculated by the second internal pressure calculation unit 112, in a state in which operation of the collection and returning pump 100 is stopped during the collection operation and during the returning operation of the first cycle. The calibration determining unit 116 determines whether or not calibration of the first calibration curve data 118 is necessary.

Next, operations of the blood component collection system 10 according to the present embodiment, which is configured in the manner described above, will be described.

As a preparation (set-up) for collecting blood components from a blood donor using the blood component collection system 10 shown in FIG. 1, the blood collection circuit set 12 is attached to the centrifugal separation device 14. More specifically, the cassette 28 is mounted in the cassette mounting unit 78, and the blood treatment unit 16 is attached to the rotor 18a. On the other hand, the blood collecting needle 20 pierces and is inserted into the blood donor.

Figure 4:
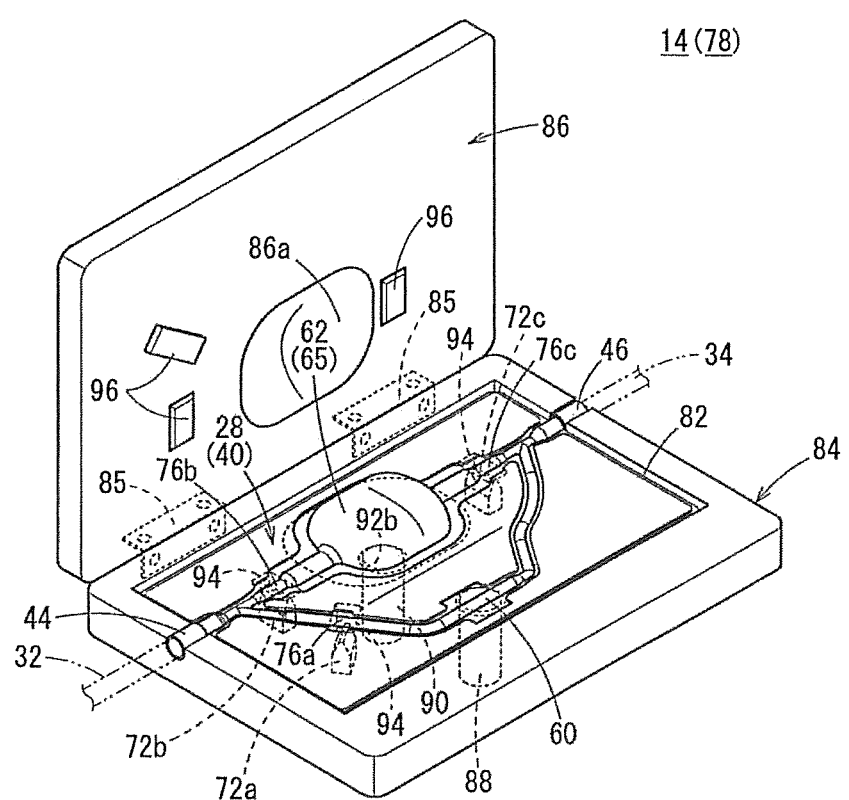
FIG. 4 is a perspective view of a cassette mounting unit in a state with the blood component collection cassette placed therein.

When the cassette 28 is mounted in the cassette mounting unit 78, as shown in FIG. 4, at first, the cassette 28 is mounted in the cassette mounting groove 82. In addition, by closing the lid 86, the cassette 28 is placed in a state of being held between the lid 86 and the attachment base 84. As a result, the first pressed portion 60 and the second pressed portion 62 of the cassette 28 are pressed respectively by the first load detecting unit 88 and the second load detecting unit 90, and are placed in a state of being slightly elastically deformed. Further, the plurality of clamp action members 76 of the cassette 28 are placed in facing relation with respect to the plurality of clamps 72.

When a command is issued by operation of a user with respect to the centrifugal separation device 14 shown in FIG. 1 in order to initiate operations, in the centrifugal separation device 14, under the action of the ACD solution transfer pump 98, priming with the ACD solution is carried out. More specifically, during priming, the ACD solution is introduced from the ACD solution bag 24a into the blood line 42 inside the cassette 28 via the ACD solution transfer tube 23, and at a stage at which it is detected by a non-illustrated line sensor disposed externally of the cassette 28 that the ACD solution has come into close proximity to the first port 43a, priming with the ACD solution is completed.

Next, by rotating the rotor 18a, the centrifugal separation device 14 applies a centrifugal force to the blood treatment unit 16 that is attached to the rotor 18a, and together therewith, by operation of the collection and returning pump 100, blood (whole blood) from the blood donor is extracted and introduced into the blood treatment unit 16 (blood collection operation or collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the blood donor (blood returning operation or returning operation). At this time, since foreign substances such as blood clumps and the like contained within the remaining blood components are trapped by the filter member 70 provided in the blood returning line 42b of the cassette 28, any risk of such foreign matter being returned to the blood donor can be reduced. The cycle of the aforementioned blood collection operation and blood returning operation is performed a plurality of times.

During operation of the blood component collection system 10, the clamps 72 (see FIG. 3) of the centrifugal separation device 14 are operated in the following manner.

Figure 5:
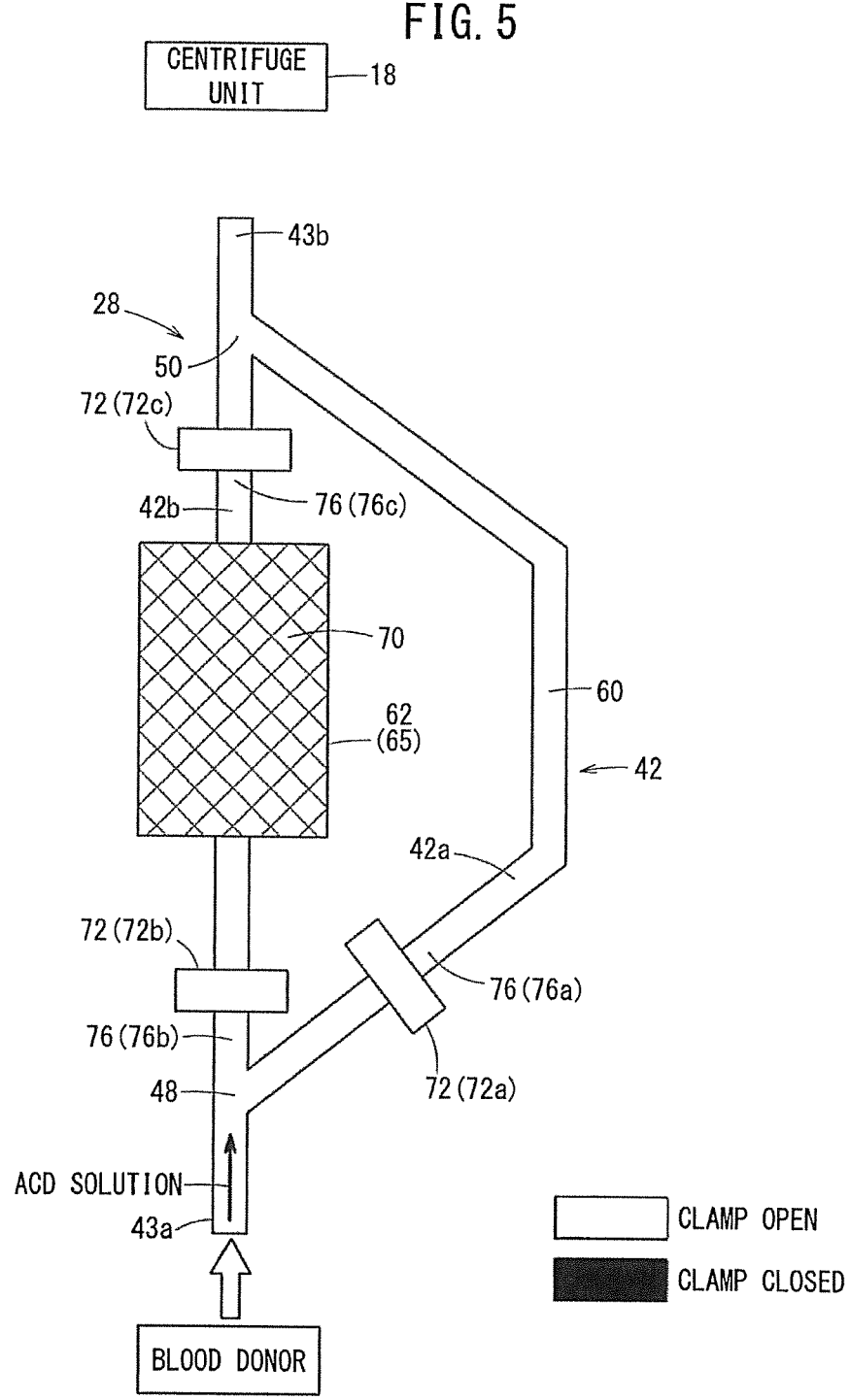
FIG. 5 is a first explanatory diagram illustrating the operation of clamps.

As shown in FIG. 5, when priming with the ACD solution is carried out, the clamps 72a, 72b, and 72c are opened. In addition, in this state, priming with the ACD solution is terminated at a stage at which it is detected by a non-illustrated line sensor outside the cassette 28 in the immediate vicinity of the first port 43a that the ACD solution has arrived in close proximity to the first port 43a.

Figure 6:
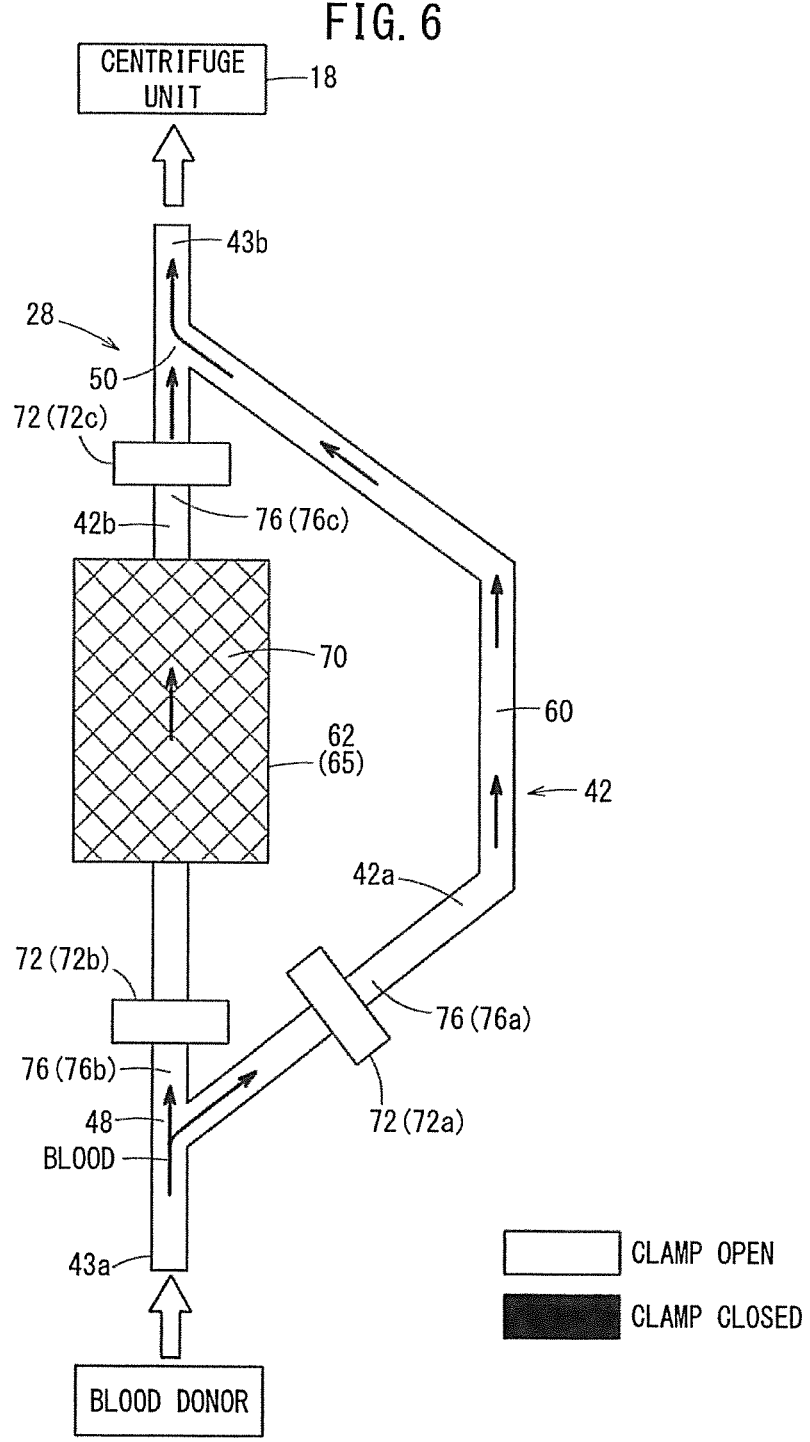
FIG. 6 is a second explanatory diagram illustrating the operation of clamps.

Next, when blood collection is performed for the first time, as shown in FIG. 6, the state in which the clamps 72*a*, 72*b*, and 72*c* are opened is maintained. In addition, in this state, blood from the blood donor is introduced into the blood line 42 of the cassette 28, and all of the air inside the circuit of the cassette 28 is pushed out by the blood into the blood treatment unit 16.

Figure 7:
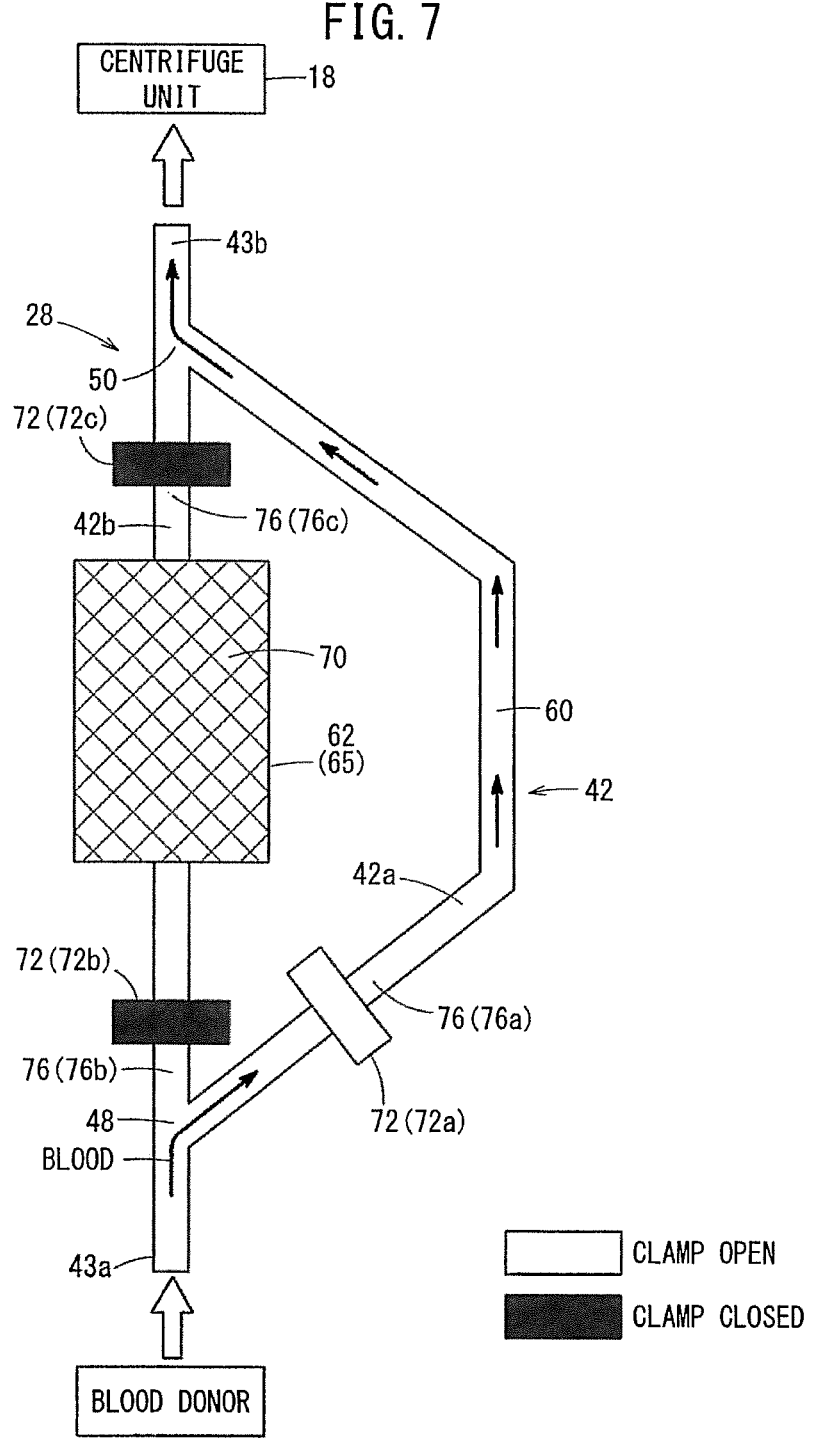
FIG. 7 is a third explanatory diagram illustrating the operation of clamps.

During the course of initial blood collection, as shown in FIG. 7, by closing the clamps 72*b* and 72*c*, the blood returning line 42*b* is closed. Consequently, a negative pressure is prevented from acting on the filter accommodating unit 65 and blocking the filter accommodating unit 65.

Figure 8:
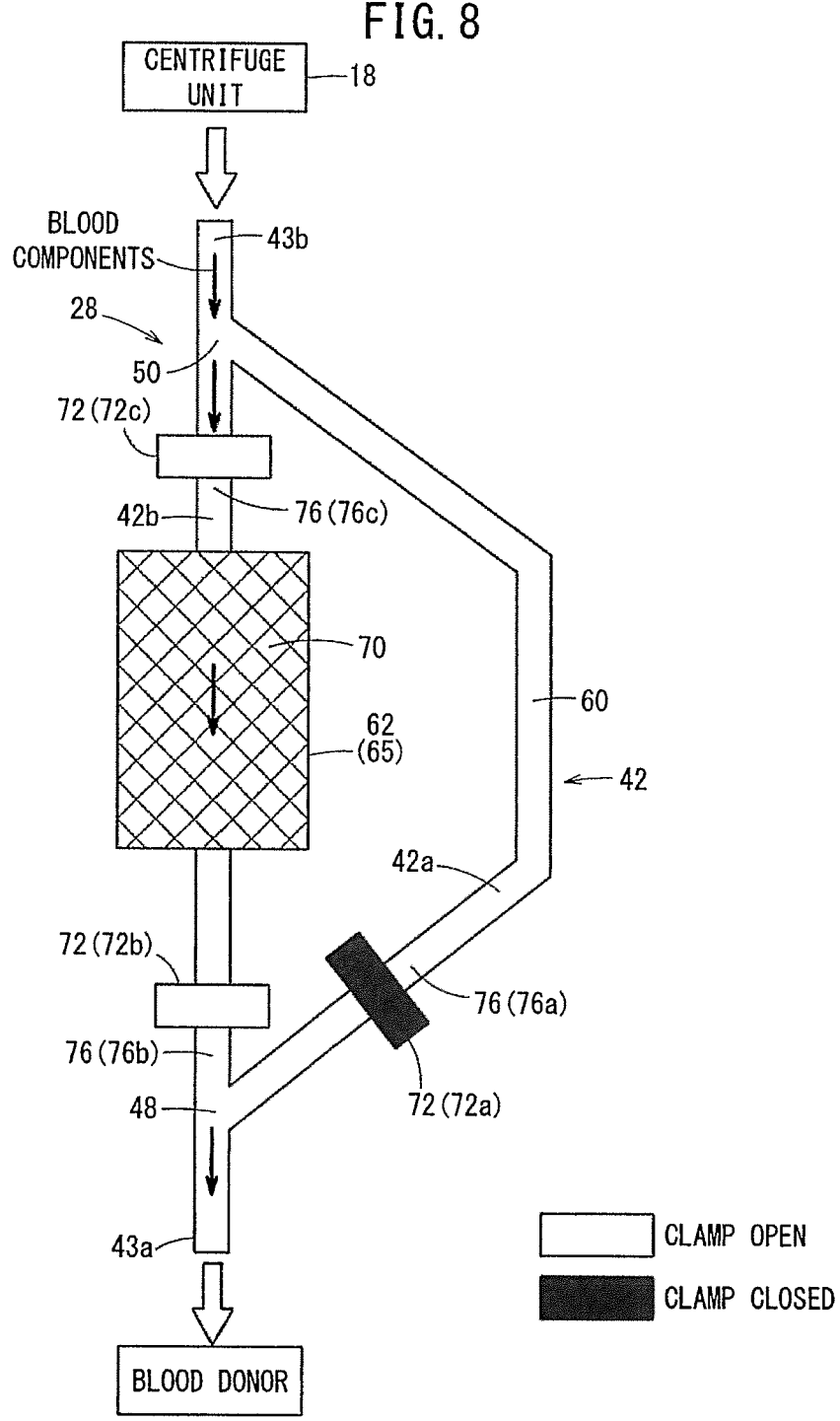
FIG. 8 is a fourth explanatory diagram illustrating the operation of clamps.

Next, when return of the blood components to the blood donor is carried out, as shown in FIG. 8, the clamp 72*a* is closed, and the clamps 72*b* and 72*c* are opened. Thus, the blood collection line 42*a* is closed, whereas the blood returning line 42*b* is opened. Accordingly, when the blood components pass through the filter member 70, clotted blood contained within the blood components is trapped in the filter member 70. Since the blood collection line 42*a* is closed, foreign matter cannot be returned to the blood donor via the blood collection line 42*a*.

Figure 9:
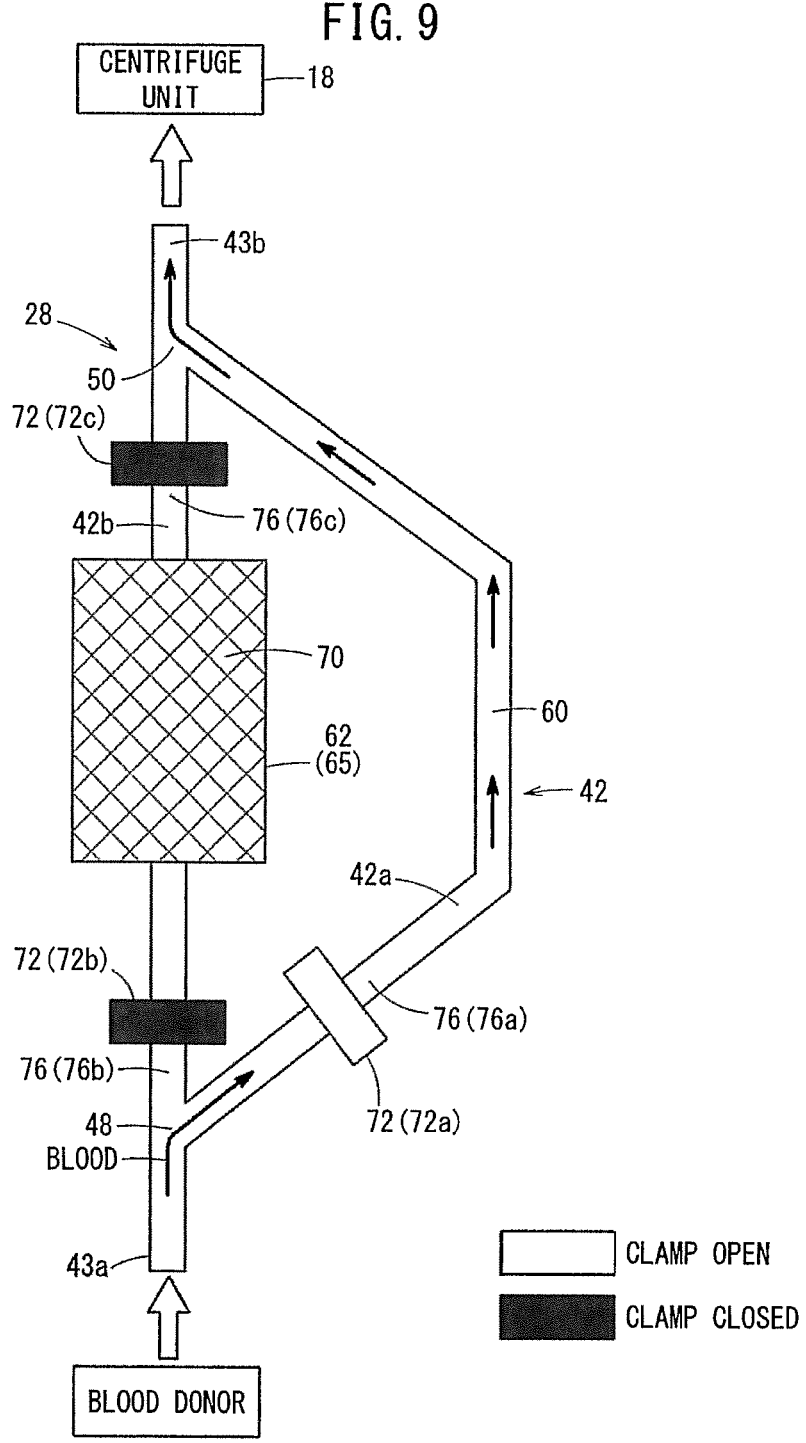
FIG. 9 is a fifth explanatory diagram illustrating the operation of clamps.

Next, when second and subsequent blood collections are carried out, as shown in FIG. 9, the clamps 72*b* and 72*c* are closed, and the clamp 72*a* is opened. Thus, the blood returning line 42*b* is closed, whereas the blood collection line 42*a* is opened. Accordingly, from among the blood collection line 42*a* and the blood returning line 42*b*, blood is transferred via only the blood collection line 42*a* to (the centrifuge unit 18 of) the blood treatment unit 16. Thereafter, return of the blood (see FIG. 8) is carried out again. Collection of blood and return of the blood in this manner are repeated a plurality of times.

In addition, when return of the blood is performed for the last time, as shown in FIG. 8, the clamp 72*a* is closed, and the clamps 72*b* and 72*c* are opened.

Next, a flow path internal pressure acquisition method in which the blood component collection system 10 is used will be described with reference to the flowchart shown in FIG. 10. The flowchart of FIG. 10 is repeatedly executed at predetermined time intervals.

Figure 10:
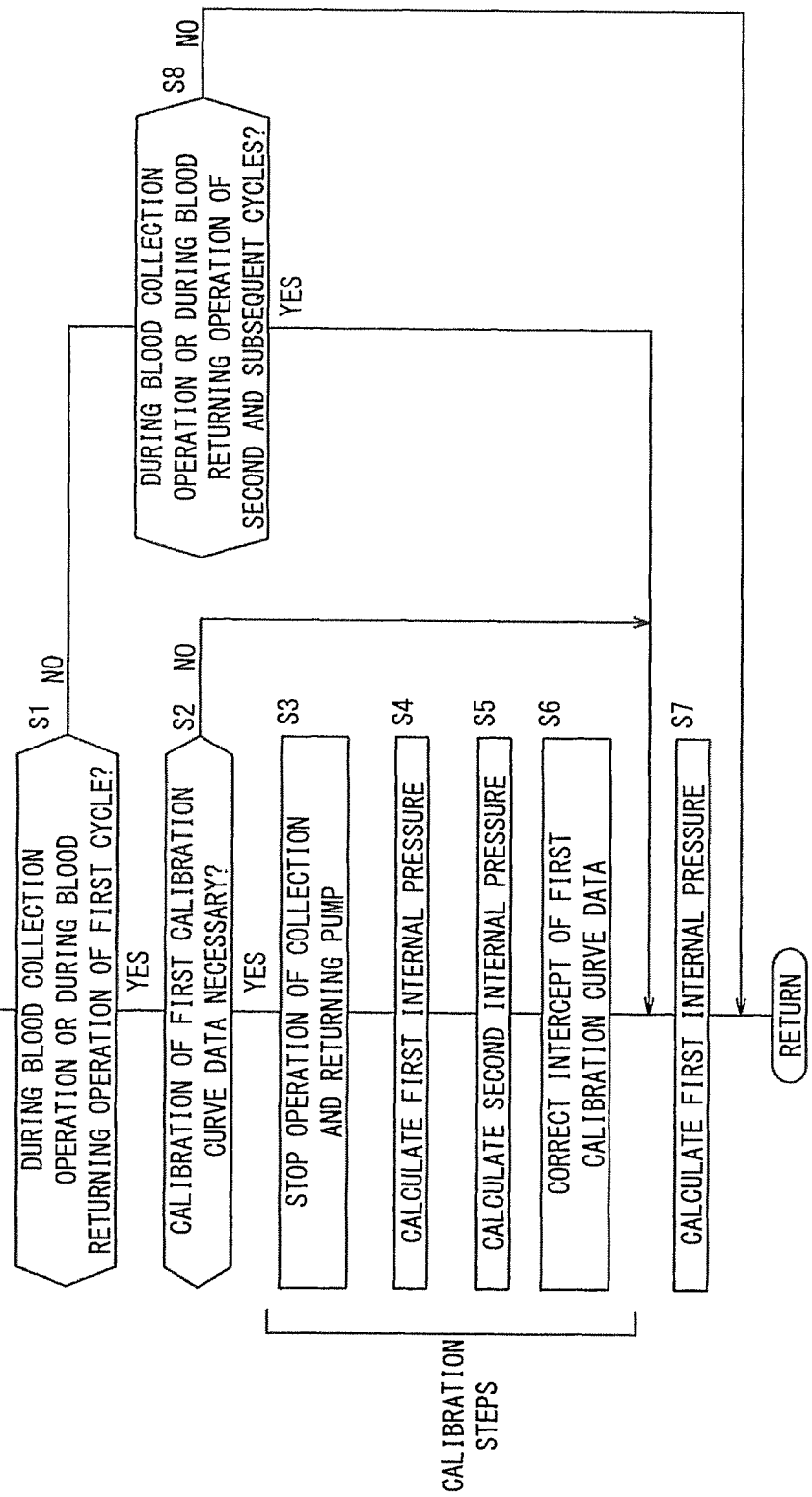
FIG. 10 is a flowchart for describing a flow path internal pressure acquisition method according to an embodiment of the present invention.

First, in step S1 (collection and returning determination step) of FIG. 10, the blood collection and blood returning determination unit 108 determines whether or not the blood collection operation or the blood returning operation of the first cycle is in progress. It should be noted that during the blood collection operation and during the blood returning operation, the collection and returning pump 100 is in operation. In the case it is determined by the blood collection and blood returning determination unit 108 that the blood collection operation or the blood returning operation of the first cycle is in progress (step S1: YES), then in step S2 (calibration determining step), the calibration determining unit 116 determines whether or not it is necessary to calibrate the first calibration curve data 118.

More specifically, for example, in each of during the blood collection operation and during the blood returning operation of the first cycle, the calibration determining unit 116 determines whether or not it is necessary to calibrate the first calibration curve data 118 in such a manner that the first calibration curve data 118 is calibrated a predetermined number of times (for example, one time). The number of times that calibration of the first calibration curve data 118 is performed in each of during the blood collection operation and during the blood returning operation of the first cycle can be set arbitrarily.

In the case it is determined by the calibration determining unit 116 that calibration of the first calibration curve data 118 is necessary (step S2: YES), then the calibration steps (step S3 to step S6) are carried out.

Figure 11:
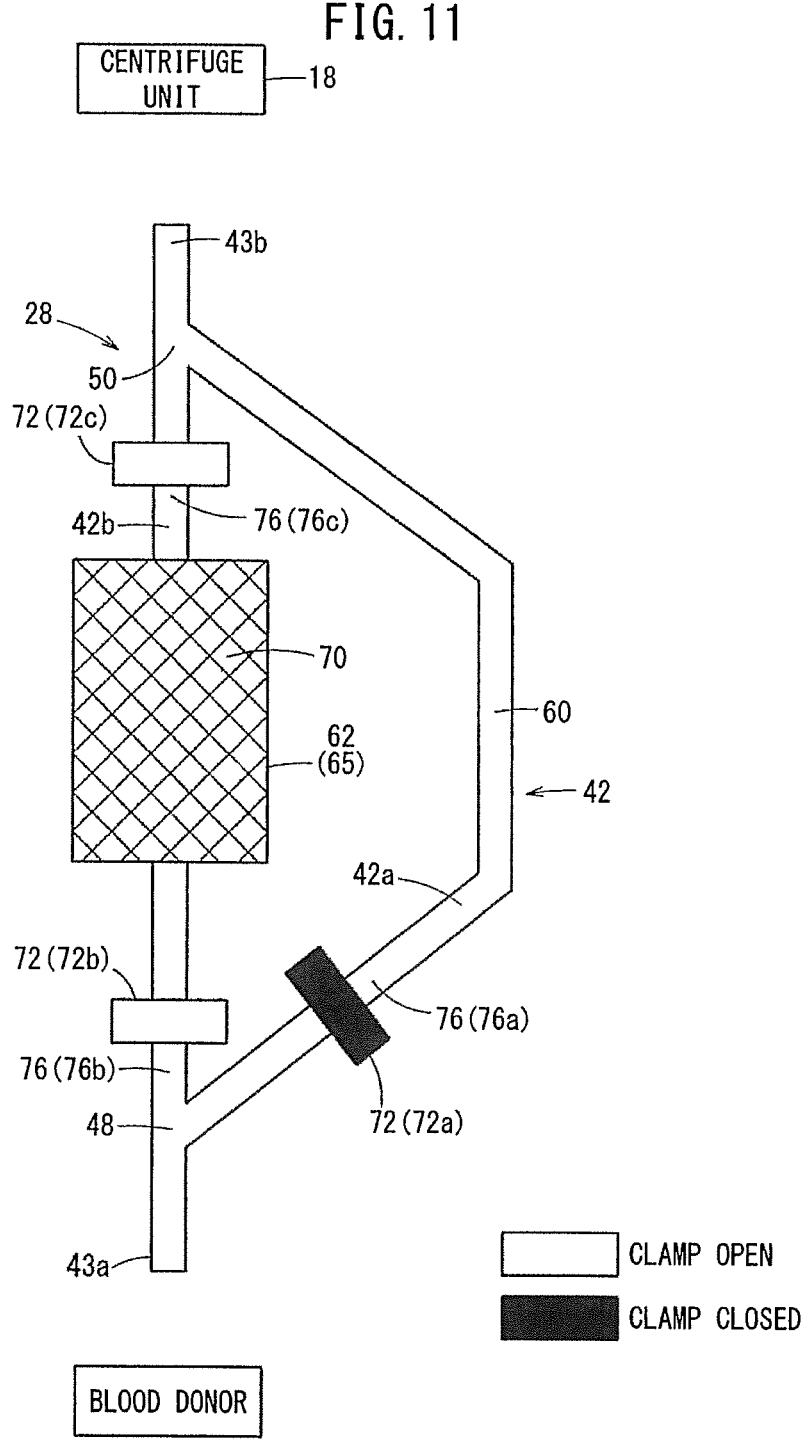
FIG. 11 is an explanatory diagram of a calibration step.

More specifically, in step S3 (pump stopping step), the pump control unit 104 terminates operation of the collection and returning pump 100. Consequently, after an elapse of from two to three seconds from terminating operation of the collection and returning pump 100, the circuit internal pressure (in the blood collection line 42*a* and the blood returning line 42*b*) becomes 0 mmHg or a value in close proximity thereto. Stated otherwise, the internal pressure of the blood collection line 42*a* and the internal pressure of the blood returning line 42*b* become equal. At this time, in either case of it being during the blood collection operation or during the blood returning operation, the clamp 72*a* is opened, and the clamps 72*b* and 72*c* are closed (see FIG. 11).

Then, in step S4 (first internal pressure calculation step), the first internal pressure calculation unit 110 calculates the first internal pressure. More specifically, in a state in which blood is not flowing through the blood collection line 42*a*, the first load detecting unit 88 presses on the first pressed portion 60, and measures the load that accompanies pressing of the first pressed portion 60. In addition, the first internal pressure calculation unit 110 calculates the internal pressure (first internal pressure) of the first pressed portion 60 on the basis of the first detection signal from the first load detecting unit 88 and the first calibration curve data 118.

Further, in step S5 (second internal pressure calculation step), the second internal pressure calculation unit 112 calculates the second internal pressure. More specifically, in a state in which blood is not flowing through the blood returning line 42*b*, the second load detecting unit 90 presses on the second pressed portion 62, and measures the load that accompanies pressing of the second pressed portion 62. In addition, the second internal pressure calculation unit 112 calculates the internal pressure (second internal pressure) of the second pressed portion 62 on the basis of the second detection signal from the second load detecting unit 90 and the second calibration curve data 120.

Figure 12:
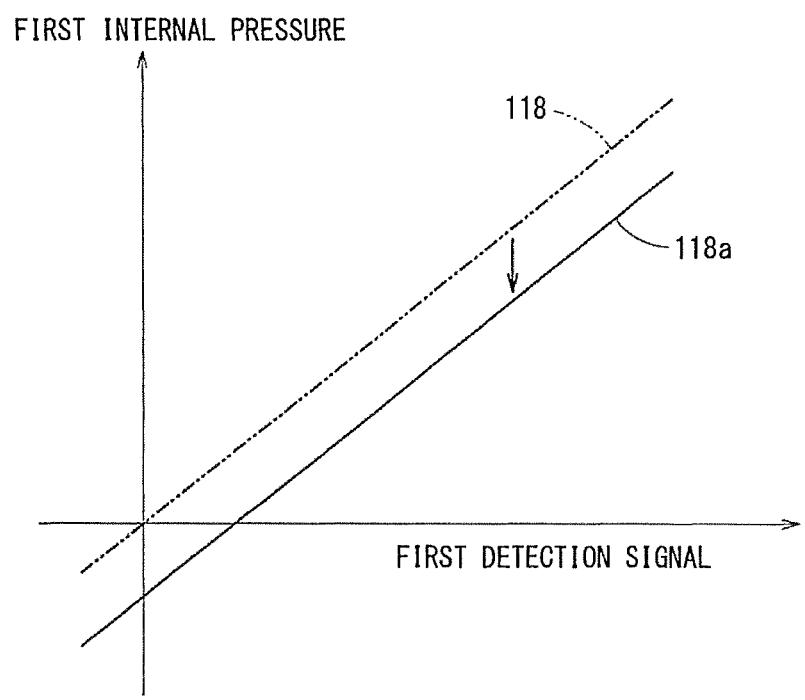
FIG. 12 is a graph for describing a correction of an intercept of first calibration curve data.

Subsequently, in step S6 (correction step), the correction unit 114 corrects the intercept of the first calibration curve data 118 (see FIG. 12) in a manner so that the first internal pressure calculated by the first internal pressure calculation unit 110 becomes equal to the second internal pressure calculated by the second internal pressure calculation unit 112. Consequently, the first calibration curve data 118*a* for which the intercept thereof has been corrected is obtained. The first calibration curve data 118 is overwritten by the first calibration curve data 118*a* and stored in the storage unit 106.

Thereafter, in step S7, the first internal pressure calculation unit 110 calculates the first internal pressure on the basis of the first detection signal and the first calibration curve data 118*a*. At this time, the first internal pressure becomes a negative pressure if it is during the blood collection operation, and becomes a positive pressure if it is during the blood returning operation. Moreover, in step S7, if it is during the blood returning operation, the second internal pressure calculation unit 112 may calculate the second internal pressure, and the calculated second internal pressure may be used as the circuit internal pressure. After step S7, the process of the flowchart of FIG. 10 is brought to an end.

In the case it is determined by the calibration determining unit 116 that calibration of the first calibration curve data 118 is not required (step S2: NO), then in step S7, the first internal pressure is calculated.

In the case that the blood collection and blood returning determination unit 108 determines that it is not during the blood collection operation or during the blood returning operation of the first cycle (step S1: NO), then in step S8, the blood collection and blood returning determination unit 108 determines whether or not it is during the blood collection operation or during the blood returning operation of the second and subsequent cycles.

In the case it is determined by the blood collection and blood returning determination unit 108 that it is during the blood collection operation or during the blood returning operation of the second and subsequent cycles (step S8: YES), then in the above-described step S7, the first internal pressure is calculated. On the other hand, in the case it is determined by the blood collection and blood returning determination unit 108 that it is not during the blood collection operation or during the blood returning operation of the second and subsequent cycles (step S8: NO), then the process of the flowchart of FIG. 10 is brought to an end.

In this case, the blood component collection system 10 and the flow path internal pressure acquisition method according to the present embodiment exhibit the following effects.

The first internal pressure calculation unit 110 calculates the first internal pressure of the first pressed portion 60 on the basis of the first detection signal from the first load detecting unit 88 and the first calibration curve data 118. The second internal pressure calculation unit 112 calculates the second internal pressure of the second pressed portion 62 on the basis of the second detection signal from the second load detecting unit 90 and the second calibration curve data 120. The correction unit 114 corrects the intercept of the first calibration curve data 118 in a manner so that the first internal pressure becomes equal to the second internal pressure, in a state in which operation of the collection and returning pump 100 is stopped during the collection operation and during the returning operation of the first cycle.

In accordance with this feature, the first internal pressure (negative pressure and positive pressure) which is a circuit internal pressure can be accurately measured by the first internal pressure calculation unit 110. The calculated first internal pressure (circuit internal pressure), for example, ranges from −300 mmHg to 500 mmHg.

Figure 13A:
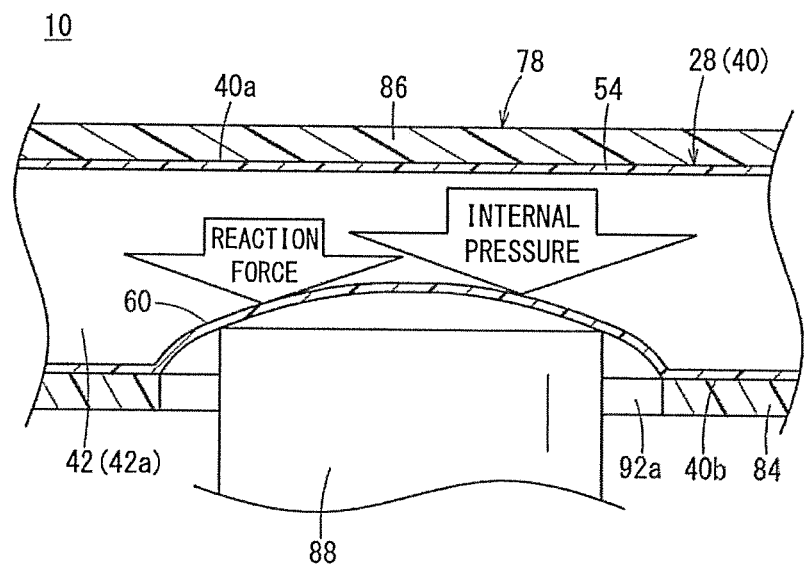
FIG. 13A is a diagram for describing load detection at a positive pressure and FIG. 13B is a diagram for describing load detection at a negative pressure.
Figure 13B:
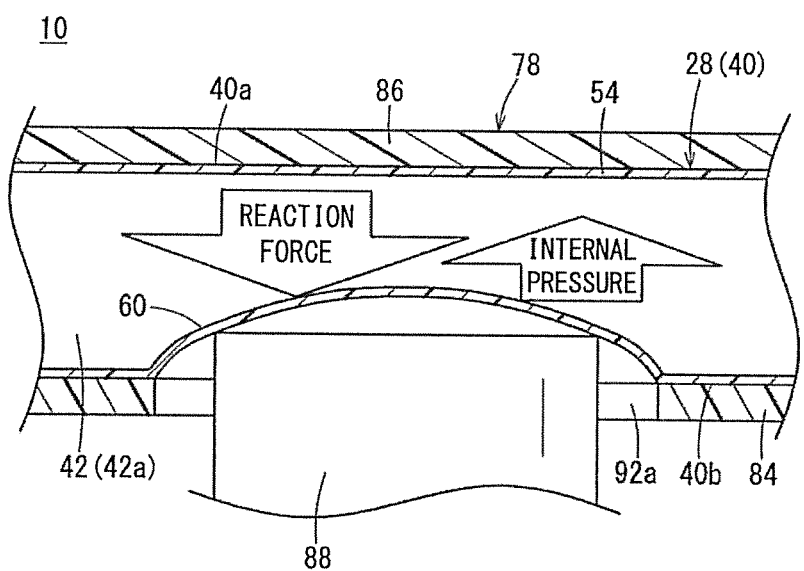

More specifically, in the case that the collection and returning pump 100 is in operation during the blood collection operation or the blood returning operation, by the first load detecting unit 88, a load is detected which is the sum of the internal pressure (circuit internal pressure) of the blood collection line 42a through which the blood flows, and the reaction force of the first pressed portion 60 (a restorative force accompanying deformation of the first pressed portion 60). That is, in the case that the circuit internal pressure is a positive pressure, as shown in FIG. 13A, the load that acts on the first load detecting unit 88 (the pressing force from the first pressed portion 60) is obtained simply by adding the circuit pressure and the reaction force. On the other hand, in the case that the circuit internal pressure is a negative pressure, as shown in FIG. 13B, the load that acts on the first load detecting unit 88 is obtained simply by subtracting the absolute value of the circuit pressure from the reaction force. In addition, the first internal pressure (circuit internal pressure) can be calculated from the first calibration curve data 118, which is indicative of a relationship between the first detection signal from the first load detecting unit 88 and the first internal pressure, and the first detection signal.

Figure 14:
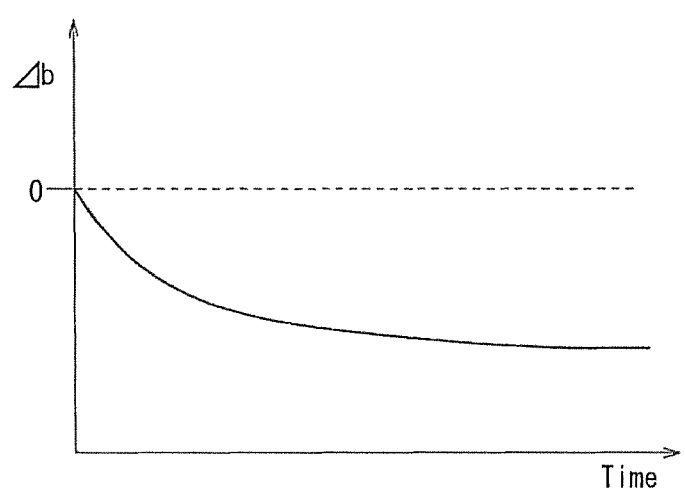
FIG. 14 is a diagram for describing a timewise change in a reaction force.

However, as shown in FIG. 14, the reaction force of the first pressed portion 60 decreases over time. In FIG. 14, there is shown an image of a temporal change (Δb) of the reaction force of the first pressed portion 60 in the case that the initial reaction force is zero. The reason that the reaction force of the first pressed portion 60 decreases over time in this manner is due to the fact that creep deformation occurs accompanying continuation of a state in which the first pressed portion 60 is pressed by the first load detecting unit 88. Accordingly, when a fixed value that does not change over time is used as the reaction force of the first pressed portion 60, the measurement accuracy of the first internal pressure is lowered. In particular, at the time of blood collection and at the time of blood returning in the first cycle, since the amount of creep deformation of the first pressed portion 60 is large, it is likely for the measurement accuracy of the first internal pressure to be lowered.

On the other hand, since the second pressed portion 62 has a flow path cross-sectional area which is greater than the flow path cross-sectional area of the first pressed portion 60, creep deformation is less likely to occur in comparison with the first pressed portion 60. In other words, the second internal pressure calculation unit 112 is capable of relatively accurately calculating the second internal pressure (positive pressure) of the second pressed portion 62.

In addition, in the blood component collection system 10, the intercept of the first calibration curve data 118 is corrected in a manner so that the first internal pressure calculated by the first internal pressure calculation unit 110 becomes equal to the second internal pressure calculated by the second internal pressure calculation unit 112, in a state in which operation of the collection and returning pump 100 is stopped during the collection operation and during the returning operation of the first cycle. In accordance with this feature, any measurement error of the first detection signal due to creep deformation of the first pressed portion 60 can be canceled by the first calibration curve data 118a for which the intercept thereof has been corrected. Accordingly, the circuit internal pressure (negative pressure and positive pressure) can be accurately measured by the first internal pressure calculation unit 110.

The first line forming member 54 forms the blood collection line 42a and together therewith includes the first pressed portion 60, and the second line forming member 64 forms the blood returning line 42b and together therewith includes the second pressed portion 62. In accordance with this feature, it is possible to suppress any influence that deformation of the first pressed portion 60 exerts on the second pressed portion 62.

The second pressed portion 62 is the filter accommodating unit 65 in which there is accommodated the filter member 70 that separates a predetermined component (clotted blood or blood clumps) from within the blood components at the time of the returning operation. In accordance with this feature, since the second pressed portion 62 can serve in a dual manner as the filter accommodating unit 65, the structure of the cassette 28 can be made compact. Further, the number of operations performed by the operator (a process to attach the filter member 70) is reduced, and usability is enhanced.

The blood line 42 further includes the first coupling member 48 which couples one end portion 42a1 of the collection line 42a and one end portion 42b1 of the returning line 42b to each other, and the second coupling member 50 which couples the other end portion 42a2 of the collection line 42a and the other end portion 42b2 of the returning line 42b to each other. In accordance with this feature, the structure of the cassette 28 can be made more compact.

The present invention is not limited to the above-described configuration. For example, the first calibration curve data 118 and the second calibration curve data 120 may be stored in a server provided separately from the centrifugal separation device 14. In this case, by way of communication therewith, the control unit 102 can acquire the first calibration curve data 118 and the second calibration curve data 120 that are stored in the server. The second pressed portion 62 may also be provided in the first line forming member 54.

In the blood component collection system 10 and the flow path internal pressure acquisition method, correction of the intercept of the first calibration curve data 118 may be performed only during the blood collection operation of the first cycle. Further, in the blood component collection system 10 and the flow path internal pressure acquisition method, correction of the intercept of the first calibration curve data 118 may be performed only during the blood returning operation of the first cycle. Furthermore, correction of the intercept of the first calibration curve data 118 may be performed only once or may be performed a plurality of times.

In the blood component collection system 10 and the flow path internal pressure acquisition method, before carrying out the blood collection operation of the first cycle after the priming process of the blood line 42 is performed by operation of the collection and returning pump 100, the intercept of the first calibration curve data 118 may be corrected in a manner so that the first internal pressure calculated by the first internal pressure calculation unit 110 in a state in which operation of the collection and returning pump 100 is stopped becomes equal to the second internal pressure calculated by the second internal pressure calculation unit 112 (pre-collection calibration step). In this case, during at least one of the blood collection operation and the blood returning operation of the first cycle, the intercept of the first calibration curve data 118a after correction thereof is further corrected. Consequently, the first internal pressure can be measured with higher accuracy.

The first load detecting unit 88 may measure the first internal pressure without pressing on a wall portion of the first applied load measurement unit. The second load detecting unit 90 may measure the second internal pressure without pressing on a wall portion of the second applied load measurement unit.

The present invention is not limited to the above-described embodiments, and various modifications may be adopted within a range that does not depart from the essence and gist of the present invention.

The invention claimed is:

1. A flow path internal pressure acquisition method in which there is used a biological component collection system equipped with a separation device having a first load detecting unit and a second load detecting unit and adapted to separate a biological component from a biological liquid, a biological component collection device configured to be attachable to the separation device and having a biological liquid line formed therein through which the biological liquid or the biological component flows, and a collection and returning pump, the method comprising
performing a plurality of times a cycle including a collection operation for
collecting a desired biological component in the biological liquid by allowing the biological liquid to flow from a donor through the biological liquid line to the separation device under an action of the collection and returning pump, and
a returning operation for returning remaining biological components to the donor from the separation device through the biological liquid line under the action of the collection and returning pump;
measuring a first load through a soft wall of the biological component collection device at a first wall portion; and
measuring a second load through said soft wall at a second wall portion;
the flow path internal pressure acquisition method further comprising:
a collection and returning determination step of determining whether or not it is during a collection operation or during a returning operation of a first cycle; and
a calibration step of performing calibration of first internal pressure calculation data, for a case in which, in the collection and returning determination step, it is determined that it is during the collection operation or during the returning operation of the first cycle;
and in the calibration step, there are performed:
a pump stopping step of stopping the collection and returning pump;
a first internal pressure calculation step of calculating a first internal pressure on the basis of said first measured load and first internal pressure calculation data in a state in which the collection and returning pump is stopped;
a second internal pressure calculation step of calculating a second internal pressure on the basis of said second measured load and second internal pressure calculation data in a state in which the collection and returning pump is stopped; and
a correction step of correcting the first internal pressure calculation data in a manner so that the first internal pressure calculated by the first internal pressure calculation step becomes equal to the second internal pressure calculated by the second internal pressure calculation step.

2. The flow path internal pressure acquisition method according to claim 1, further comprising:
a pre-collection calibration step of performing calibration of the first internal pressure calculation data prior to performing the collection operation of the first cycle after having performed a priming process of the biological liquid line by operating the collection and returning pump;
wherein, in the pre-collection calibration step, the same processes as those of the calibration step are performed.

* * * * *